United States Patent [19]

Aktogu et al.

[11] Patent Number: 5,034,396
[45] Date of Patent: Jul. 23, 1991

[54] METHOD OF TREATING DEPRESSION WITH OPTICALLY ACTIVE ISOMERS OF 20,21-DINOREBURNAMENINES

[75] Inventors: Nurgün Aktogu, Le Plessis Robinson; Francois Clemence; Claude Oberlander, both of Paris, all of France

[73] Assignee: Roussel Uclaf, Paris, France

[21] Appl. No.: 271,733

[22] Filed: Nov. 15, 1988

[30] Foreign Application Priority Data

Nov. 19, 1987 [FR] France ................... 87 15979

[51] Int. Cl.$^5$ ............... A61K 31/475; C07D 461/00
[52] U.S. Cl. .............................. 514/283; 546/51
[58] Field of Search ....................... 546/51; 514/283

[56] References Cited

U.S. PATENT DOCUMENTS 4,291,038  9/1987  Farcilli et al. .................. 514/283
4,501,740  2/1985  Clemence et al. .............. 514/283

FOREIGN PATENT DOCUMENTS 2590572  5/1987  France .

OTHER PUBLICATIONS

Barzaghi, et al., Arneim-Forsch./Drug Res. 36(II), nr. 10, pp. 1442–1447 (1986).
Manresa Ferreo et al., Chemical Abstracts, vol. 107(13):115839a (09/28/87).

Primary Examiner—Diana G. Rivers
Attorney, Agent, or Firm—Bierman & Muserlian

[57] ABSTRACT

A compound selected from the group consisting of optically active isomers of a racemic compound of the formula

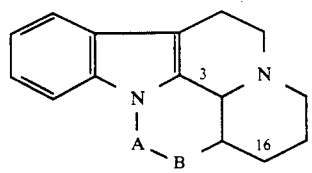

wherein the 3-hydrogen and 16-hydrogen are trans and

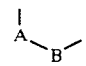

is selected from the group consisting of

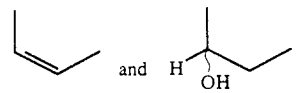

with the —OH being α or β and their non-toxic, pharmaceutically acceptable acid addition salts having antidepressant activity and an affinity for alpha$_2$ adrenergic receptors, 6 Claims, No Drawings

METHOD OF TREATING DEPRESSION WITH OPTICALLY ACTIVE ISOMERS OF 20,21-DINOREBURNAMENINES

STATE OF THE ART

French Patent No. 2,514,357 describes in Example 1 the racemic product of formula I wherein $$\underset{B}{\overset{|}{A}}\diagdown \quad is \quad \diagdown\!=\!\diagup$$

and Examples 2 and 4 of Belgium Patent No. 864,173 describe the racemic product of formula I wherein $$\underset{B}{\overset{|}{A}}\diagdown \quad is \quad H\!\!\diagdown\!\underset{OH}{\diagup}$$

Related prior art are U.S. Pat. Nos. 4,291,038 and 4,501,740, French Patent No. 2,590,572 and Arzneimittel Forshung, Vol. 36 (II), No. 10 (1986), p. 1442–1448.

OBJECTS OF THE INVENTION

It is an object of the invention to provide the optical isomers of the compounds of formula I and their non-toxic, pharmaceutically acceptable acid addition salts.

It is a further object of the invention to provide novel antidepressant compositions and to provide a novel method of relieving depression in warm-blooded animals.

These and other objects and advantages of the invention will become obvious from the following detailed description.

THE INVENTION

The novel compounds of the invention are selected from the group consisting of optically active isomers of a racemic compound of the formula

I wherein the 3-hydrogen and 16-hydrogen are trans and $$\underset{B}{\overset{|}{A}}\diagdown$$

is selected from the group consisting of $$\diagdown\!=\!\diagup \quad or \quad H\!\!\diagdown\!\underset{OH}{\diagup}$$

with the —OH being $\alpha$ or $\beta$ and their non-toxic, pharmaceutically acceptable acid addition salts.

Among the preferred compounds of formula I are those optically active isomers wherein $$\underset{B}{\overset{|}{A}}\diagdown \quad is \quad H\!\!\diagdown\!\underset{OH}{\diagup}$$

and 3 and 16 hydrogens are trans, especially (14$\alpha$, 16$\alpha$)-14,15-dihydro-20,21-dinoreburname-14-ol, (3$\alpha$,14$\alpha$)-14,15-dihydro-20,21-dinoreburnamenin-14-ol, (14$\beta$16$\alpha$) 14,15-dihydro-20,21-dinoreburnamenin-14-ol and (3$\alpha$, 14$\beta$) 14,15-dihydro-20,21-dinoreburnamenin-14-ol and those wherein $$\underset{B}{\overset{|}{A}}\diagdown \quad is \quad \diagdown\!=\!\diagup$$

and the 3 and 16-hydrogens are trans, especially (16$\alpha$) 20,21-dinoreburnamenine and (3$\alpha$) 20,21-dinoreburnamenine and their their non-toxic, pharmaceutically acceptable acid addition salts.

Examples of suitable acids for the preparation of the acid addition salts are inorganic acids such as hydrochloric acid, hydrobromic acid, hydroiodic acid, sulfuric acid, nitric acid and phosphoric acid and organic acids such as formic acid, acetic acid, propionic acid, maleic acid, formic acid, succinic acid, tartaric acid, citric acid, oxalic acid, glyoxylic acid, aspartic acid and ascorbic acid, aromatic acids such as benzoic acid, alkane sulfonic acids such as methane sulfonic acid, propane sulfonic acid, ethane sulfonic acid, alkane disulfonic acids such as methanedisulfonic acid and $\alpha,\beta$,-ethane disulfonic acid and arylsulfonic acids and aryl disulfonic acids such as benzene sulfonic acid.

The novel process of the invention for the preparation of the optically active isomers of formula I comprises reducing a trans compounds of the formula

II

3 $\alpha$-trans or

II'

16 $\alpha$-trans to obtain either the 3$\alpha$-trans compounds of formula $I_A$ or 16$\alpha$-trans compound of formula $I_A'$ wherein

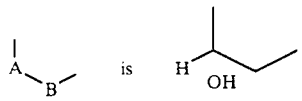

in which the OH is in the equatorial position, optionally treating the latter with acid to obtain the corresponding 3α-trans compound of formula $I_{A1}$ or 16α-trans compounds of formula $I_{A1}'$ wherein the hydroxy is in the axial position and optionally dehydrating the compounds of formulae $I_A$, $I_{A1}'$, $I_A'$ or $I_{A1}'$ to obtain the corresponding 3α-trans compound of formula $I_C$ or 16α-trans compound of formula $I_C'$ wherein

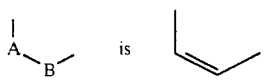

and optionally salifying the said compounds.

In a preferred mode of the process, the reduction of the products of formula II or II' is effected with a hydride such as lithium aluminium hydride or sodium aluminium diethylhydride and the acid is hydrochloric acid. The separation of the compounds of formulae $I_A$ and $I_{A1}$ and $I_A'$ may be effected by chromatography. The dehydration agent is an acid such as hydrochloric acid, hydrobromic acid, sulfuric acid, acetic acid, p-toluene sulfonic acid or methane sulfonic acid.

The novel anti-depressant compositions of the invention are comprised of an anti-depressant effective amount of at least one optically active isomer of formula I and its non-toxic, pharmaceutically acceptable acid addition salts and an inert pharmatical carrier or excipient. The compositions may be in the form of tablets, dragees, capsules, granules, suppositories, creams, gels, ointments, injectable solutions or suspensions and aerosols.

Examples of suitable excipients are talc, arabic gum, lactose, starch, magnesium stearate, cocoa butter, aqueous and non-aqueous vehicles, animal and vegetable fatty substances, paraffinic derivatives, glycols, various wetting agents, emulsifiers and dispersants and preservatives.

The compositions have an important affinity for alpha$_2$ adrenergic receptors with an important dissociation of the affinity for the alpha$_2$ receptor between the two enantiomers of each racemic product. The optically active products of the invention offer also useful anti-amnesiant, anti-depressive, neuronal protecting, anti-anoxic, anti-ischemic, nootropic (anti-amnesiant effect in a passive avoidance and reversion of an amnesic deficit after central cholinergic lesion).

The compositions are useful in the treatment of cerebral insufficiencies of anoxic and ischemic origin and in disorders of memory, attention and vigilance as well as anti-depressants.

The method of the invention for the treatment of depression in warm-blooded animals, including humans, comprises administering to warm-blooded animals or anti-depressant effective amount of at least one optical isomer of formula I or its non-toxic, pharmaceutically acceptable acid addition salts. The compounds may be administered orally, rectally, topically or parenterally and the usual daily dose is 0.133 to 2.66 mg/kg depending on the condition treated, the specific compound and the method of administration.

The compounds of formulae II and II' are described in Belgium patent No. 764,166.

In the following examples there are described several preferred embodiments to illustrate the invention. However, it should be understood that the invention is not intended to be limited to the specific embodiments.

EXAMPLE 1

(14β,16α)-14,15-dihydro-20,21-dinoreburnamenin-14-ol 10.8 g of (16α) (+) 20,21-dinoreburnamenin-14(15H)-one were dissolved in 110 ml of anhydrous toluene, and over ten minutes under an inert atmosphere, 18.9 ml of diethyl-aluminium sodium dihydride at 25% in toluene were added followed by stirring for one hour at ambient temperature. The mixture was then hydrolyzed by the addition of 20 ml of 5N sodium hydride and was heated at 90° C. for two hours. The toluene was distilled off, and simultaneously 100 ml of water were introduced. After returning to ambient temperature, the product obtained was separated, washed with water and dried under reduced pressure to obtain 10.7 g of the expected product which after crystallization from methanol, melted at 254° C. and had a specific rotation of $[\alpha]_D = +36° \pm 1°$ (c=0.6% in DMF).

Circular dichroism (dioxane): Max.: 225 nm, $\Delta\epsilon = -8$; Max.: 237 nm, $\Delta\epsilon = +9.5$; Max.: 280 nm, $\Delta\epsilon = -2$.

NMR Spectrum (pyridine) 250 MHz ppm

Possible structure with OH equatorial
OH axial not detected.

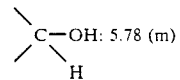

EXAMPLE 2

(3α, 14α) 14,15-dihydro-20,21-dinoreburnamenin-14-ol

Using the procedure of Example 1, 15 g of (3α) (−) 20,21 dinoreburnamenin-14(15H)-one were reacted to obtain 15 g of the expected product containing very little of the product with OH axial. After crystallization from methanol, the product melted at 254° C. and had a specific rotation of $[\alpha]_D = +32.5° \pm 1°$ (c=1% in DMF).

Circular dichroism (dioxane): Max.: 227 nm, $\Delta\epsilon = +10$; Max.: 238 nm, $\Delta\epsilon = -10$; Max.: 288 nm, $\Delta\epsilon = +2$.

NMR Spectrum (pyridine) 250 MHz, ppm

Possible structure with OH equatorial
OH axial not detected.

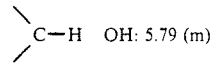

EXAMPLE 3

(14α, 16α) 14,15-dihydro-20,21-dinoreburnamenin-14-ol 2.75 g of the product of Example 1 were suspended in 55 ml of 2N hydrochloric acid and the suspension was heated for 90 minutes at 50° C. 55 ml of iced water were added to the solution, which was made alkaline by addition of 10 ml of 22° Be ammonia and stirred for 15 minutes at ambient temperature. The precipitate was separated, washed with water and dried at 30° C. under reduced pressure to obtain 2.75 g of product (mixture of axial and equatorial OH). The latter was chromatographed on silica under pressure and eluted with a mixture of ethyl acetate - methanol - ammonia (97-3-0.3) to obtain 1.70 g of the expected product (OH axial) melting at 234° C. and having a specific rotation of $[\alpha]_D = +150° \pm 2°$ (c=1% in DMF)

Circular dichroism (dioxane): Max.: 230 nm, $\Delta\epsilon = +19$; Max.: 290 nm, $\Delta\epsilon = -1.75$.

NMR Spectrum (pyridine) 250 MHz, ppm

Possible structure with OH axial
isomer OH equatorial not detected.

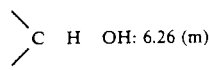
C H OH: 6.26 (m)

EXAMPLE 4

(3α, 14β) 14,15-dihydro-20,21-dinoreburnamenin-14-ol

Using the procedure of Example 3, 13.3 g of the product of Example 2 were reacted to obtain 7.7 g f product (OH axial) melting at 234° C. and having a specific rotation of $[\alpha]_D = -152.5° \pm 2.5°$ (c=1% in DMF).

Circular dichroism (dixoane): Max.: 228 nm, $\Delta\epsilon = -20$; Max.: 290 nm, $\Delta\epsilon = +1.5$.

NMR Spectrum (pyridine) 250 MHz, ppm

—C H OH: 6.23 (m)

EXAMPLE 5

(3α) 20,21-dinoreburnamenine 1.2 g of the product of Example 2 were suspended in 24 ml of anhydrous toluene and 1% of p-toluenesulfonic acid was added. The mixture was refluxed for 4 hours and after taking to dryness, the dry extract was taken up in 50 ml of ethyl acetate. The insolule matter was filtered off and the filtrate was concentrated to dryness. The residue was chromatographed on silica and eluted with a mixture of methylene chloride and acetone (1-1) to obtain 0.610 g of the expected product melting at 139° C. and having a specific rotation of $[\alpha]_D = +445.5° \pm 5°$ (c=1% in CHCl₃).

Circular dichroism (ethanol): Max.: 257 nm, $\Delta\epsilon = +33$; Infl.: 290 nm, $\Delta\epsilon = +3.5$; Infl.: 299 nm, $\Delta\epsilon = +5.7$; Infl.: 302 nm, $\Delta\epsilon = +6$; Max.: 308 nm, $\Delta\epsilon = +7.8$.

NMR Spectrum (CDCl₃) 250 MHz ppm

| Possible structure, trans function: | |
|---|---|
| ethylenes: | 5.07 (dd, j = 2 and 7.5) |
| | 6.96 (dd, j = 3 and 7.5) |
| indole: | H₃/H₆: 7.05 to 7.20 |
| | H₄/H₇: 7.32 (d) and 7.46 (d) |
| Other protons: | 1.3 to 3.2. |

EXAMPLE 6

(16α) 20,21-dinoreburnamenine

Using the procedure of Example 5, 1.2 g of the product of Example 1 were reacted to obtain 0.640 g of the expected product melting at 139° C. and having a specific rotation of $[\alpha]_D = -439° \pm 5°$ (c=1% in CHCl₃).

Circular dichroism (ethanol): Max.: 257 nm, $\Delta\epsilon = -31$; Infl.: 290 nm, $\Delta\epsilon = -32$; Infl.: 300 nm, $\Delta\epsilon = -5.3$; Max.: 307 nm, $\Delta\epsilon = -7.48$.

NMR Spectrum (CDCl₃) 250 MHz, ppm

| Possible structure, trans function: | |
|---|---|
| ethylenes: | 5.07 (dd, j = 2 and 7.5) |
| | 6.96 (dd, j = 3 and 7.5) |
| indole H₅ and H₆: | 7.05 to 7.20 |
| H₄ and H₇ | 7.32 (d) and 7.46 (d) |
| other protons: | 1.3 to 3.2. |

EXAMPLE 7

Pharmaceutical Form

Tablets were prepared containing 300 mg of the product of Example 3 and sufficient excipient of talc, magnesium stearate and aerosil for a tablet weighing 350 mg.

PHARMACOLOGICAL STUDY (1) Affinity for the alpha₂ adrenergic receptors 10 cortices removed from the brains of male rats weighing an average of 150 g were homogenized in 90 ml of sucrose 0.32M and after centrifuging the homogenized mixture at 1,000 g for 10 minutes at 0° C., the supernatant was centrifuged at 30,000 g for 10 minutes at 0° to 4° C. The new residue obtained was suspended in 480 ml of NaKPO₄ buffer, pH 7.4, 50 mM. 2 ml of the suspension were then incubated for 45 minutes at 25° C. in the presence of ³H rauwolscine at a concentration of 0.15 nM: (i) alone (ii) with increasing concentrations of the product under test, or (iii) to determine the non-specific fixation, with non-radioactive phentolamine at a concentration of 10⁻⁵M. The incubated suspensions were filtered on Whatman GF/C and the filters were washed three times with 5 ml of NaKPO₄ buffer, pH 7.4 at 0° C. The radioactivity of the filters was measured by liquid scintillation.

The affinity of the product tested for the alpha₂ adrenegic receptors was given relative to phentolamine as reference product.

CD = concentration of phentolamine inhibiting 50% of the specific fixation of the ³H rauwolscine:

CX = concentration of the product under test inhibiting 50% of the specific fixation of the ³H rauwolscine.

The relative affinity was given by the relation:

$$ARL = 100 \frac{CD}{CX}$$

and the results are as follows:

| Products of Example | ARL |
|---|---|
| 3 | 0.3 |
| 4 | 57 |
| 5 | 8 |

-continued

| Products of Example | ARL |
| --- | --- |
| 6 | 633 |

(2) Hypobaric anoxia test on mice

This consisted of measuring over a maximum duration of 3 minutes the survival time of mice placed in a 2 liter enclosure in which there was a depression of 600 mm Hg. The products were administered intraperitoneally at a volume of 0.2 ml/10 g 60 minutes before the test.

| Product of Example | Survival time |
| --- | --- |
| 3 | +37% |

(3) Test of neuronal protection in mice

A cerebral lesion was carried out on the mouse by injection in the right striatum of 2 μg of kainic acid in a volume of 0.5 μl. In the hours which followed, the injury showed itself by a seric liberation of the neuronal marker (enolase gamma-gamma) proportional to the extent of the lesion. The products were injected intraperitonally 60 minutes before the neurotoxic and the blood samples were taken 24 hours later.

| Product of Example | enolase gamma-gamma |
| --- | --- |
| 3 | −24% |

(4) Test of anti-depressive activity

The tests were carried out on groups of 5 Sprague Dawley rats and the non-conditioned animals were put for 15 minutes in a vertical perspex cylinder (diameter: 18 cm, height: 400 cm) containing water at 25° C. to a height of 15 cm (initial swimming test). They were then dried for 15 minutes in an enclosure heated to 32° C. and 24 hours later, they were replaced in the cylinder filled with water, and the total duration of the periods of immobility was measured during 5 minutes. The compound was administered intraperitonally successively 24 hours, 5 hours and a half-hour before the test. The first administration was made immediately after the first swimming test and just before replacing the animals in their breeding box. The averages of the groups treated were compared with those of the control group by the Dunnett test. Results:

| Product of Example | $DA_{50}$ mg/Kg |
| --- | --- |
| 3 | about 10 |
| 4 | about 5 |

Anti-amnesic Effect in a Passive Avoidance

Some rats were placed individually in the illuminated compartment of a box with two compartments, the other being dark. They spontaneously took refuge in the dark compartment and immediately on their entry, the rats received an electric shock (1 mA/5 sec.) from the floor grating. The animals were then divided into 3 groups: the first group (control) were not manipulated further. In the second group, the electric shock was immediately followed by the application of an amnesisting electric shock (60 mA, 0.6 ms, 0.6 s.) (electric shock control group). The third group was identical to the second, but the electric shock was immediately followed by the adminstration of the compound under test (treated group). Twenty-four hours later, the animals were replaced in the illuminated compartment of the box and the latency time of entry into the dark compartment (up to 300 seconds max.) was measured. In the controls, this time was close to 300 seconds. The electric shock controls, on the contrary, penetrated the dark compartment much more rapidly (amnesic effect). The products with an anti-amnesic effect increased the latency of entry and tended to bring it back to a value comparable to that of the controls without electric shock. The compounds of Examples 3 and 4 reversed the effect of the amnesic electric shock at doses of 0.5 and 1 mg/Kg i.p respectively.

Various modifications of the compounds and method of the invention may be made without departing from the spirit or scope thereof and it is to be understood that the invention is intended to be limited only as defined in the appended claims.

What we claimed is:

1. A method of treating depression in warm-blooded animals comprising administering to warm-blooded animals an antidepressive amount of at least one compound selected from the group consisting of optically active isomers of a racemic compound of the formula

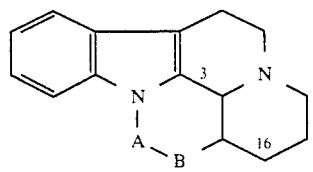

wherein the 3-hydrogen and 16-hydrogen are trans and

is selected from the group consisting of

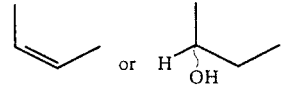

with the —OH being α or β and their non-toxic, pharmaceutically acceptable acid addition salts.

2. A method of claim 1 wherein the active compound is selected from the group consisting of (14β, 16α) 14,15-dihydro 20,21-dinoreburnamenin-14-ol and its non-toxic, pharmaceutically acceptable acid addition salts.

3. A method of claim 1 wherein the active compound is selected from the group consisting of (3α, 14β) 14,15-dihydro 20,21-dinoreburnamenin-14-ol and its non-toxic, pharmaceutically acceptable acid addition salts.

4. A method of claim 1 wherein the active compound is selected from the group consisting of (14α, 16α) 14,15-dihydro 20,21-dinoreburnamenin-14-ol and its non-toxic, pharmaceutically acceptable acid addition salts.

5. A method of claim 1 wherein the active compound is selected from the group consisting of (3α, 14α) 14,15-dihydro 20,21-dinoreburnamenin-14-ol, and its non-toxic, pharmaceutically acceptable acid addition salts.
6. A method of claim 1 wherein 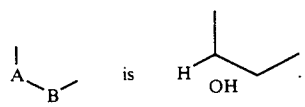 is
* * * * *